(12) United States Patent
Manolagas et al.

(10) Patent No.: US 6,660,468 B1
(45) Date of Patent: Dec. 9, 2003

(54) VITRO AND IN VIVO MODELS FOR SCREENING COMPOUNDS TO PREVENT GLUCOCORTICOID-INDUCED BONE DESTRUCTION

(75) Inventors: Stavros C. Manolagas, Little Rock, AR (US); Robert L. Jilka, Little Rock, AR (US); Robert S. Weinstein, Little Rock, AR (US); Teresita Bellido, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 0 days.

(21) Appl. No.: 09/413,958

(22) Filed: Oct. 7, 1999

Related U.S. Application Data
(60) Provisional application No. 60/105,805, filed on Oct. 27, 1998.

(51) Int. Cl.[7] .................................................. C12Q 1/00
(52) U.S. Cl. .............................................. 435/4; 435/71
(58) Field of Search ....................................... 435/4, 71

(56) References Cited

U.S. PATENT DOCUMENTS

| | | |
|---|---|---|
| 5,071,773 A | 12/1991 | Evans et al. |
| 5,189,212 A | 2/1993 | Ruenitz |
| 5,298,429 A | 3/1994 | Evans et al. |
| 5,362,720 A | 11/1994 | Labrie |
| 5,506,102 A | 4/1996 | McDonnell |
| 5,545,634 A | 8/1996 | Labrie |
| 5,554,601 A | 9/1996 | Simpkins et al. |
| 5,567,695 A | 10/1996 | Labrie |
| 5,843,934 A | 12/1998 | Simpkins et al. |
| 5,846,960 A | 12/1998 | Labrie |
| 5,877,007 A | 3/1999 | Housey |
| 6,080,779 A | 6/2000 | Gasper et al. |

FOREIGN PATENT DOCUMENTS

| | | |
|---|---|---|
| EP | 0 753 523 A1 | 1/1997 |
| WO | WO 99/54728 A2 | 10/1999 |
| WO | WO 99/61044 A1 | 12/1999 |
| WO | WO 00/19823 A1 | 4/2000 |
| WO | WO 00/20007 A1 | 4/2000 |
| WO | WO 00/20625 A1 | 4/2000 |
| WO | WO 00/37681 A1 | 6/2000 |

OTHER PUBLICATIONS

Bellows, C.G. et al., *Physiological Concentrations of Glucocorticoids Stimulate Formation of Bone Nodules from Isolated Rat Calvaria Cells in Vitro*, Endocrinology 121:4–6:1985–1992 (1987).

Bellows, C.G. et al. *Initiation and progression of mineralization of bone nodules formed in vitro: the role of alkaline phosphatase and organic phosphate*, Bone and Mineral 14: 27–40 (1991).

Bressot, C. et al. *Histomorphometric Profile, Pathophysiology, and Reversibility of Corticosteroid–induced Osteoporosis*, Metabolic Bone Disease & Related Research 1: 303–311 (1979).

Broulik, P.D. and L. Starka. *Effect of Antiandrogens Casodex and Epitestosterone on Bone Composition in Mice*, Bone 20: 473–475 (1997).

Bursch, W. et al. *Determination of the length of the histological stages of apoptosis in normal liver and in altered hepatic foci of rats*, Carcinogenesis 11: 847–853 (1990).

Chavassieux, P. et al., *Short–Term Effects of Corticosteroids on Trabecular Bone Remodeling in Old Ewes*, Bone. 20:451–455 (1997).

Conaway, H.H. et al. *Stimulation of Neonatal Mouse Calvarial Bone Resorption by the Glucocorticoids Hydrocortisone and Dexamethasone* Journal of Bone and Mineral Research 11: 1419–1429 (1996).

Cline, M., J., *Drugs and Phagocytes*, The New England Journal of Medicine 291:1187–1188 (1974).

Cope, C.L. *Synthetic Analogues* In: Adrenal Steroids and Disease (1972) Lippincott, Philadelphia, PA USA, 488–491.

Cushing, H. *The Basophil Adenomas of the Pituitary Body and their Clinical Manifestations* Bulletin of the John Hopkins Hospital, vol. 1: 137–195 (1932).

Deloffre, P. et al., *Comparison Between Bone Density and Bone Strength in Glucocorticoid–Treated Aged Ewes*, Bone. 17 (Suppl):409S–14S (1995).

Dempster, D.W., *Bone Histomorphometry in Glucocorticoid–Induced Osteoporosis*, Journal of Bone and Mineral Research. 4:137–141 (1989).

Dempster, D.W. et al., *Glucocorticoids Inhibit Bone Resporption by Isolated Rate Osteoclasts by Enhancing Apoptosis*, Journal of Endocrinology 154:397–406 (1997).

Falla, N. et al.,*Characterization of a 5–Fluorouracil–Enriched Osteoprogenitor Population of the Murine Bone Marrow*, The Journal of The American Society of Hematology. 82:3580–3591 (1993).

Fitzpatrick, L.A. *Glucocorticoid–Induced Osteoporosis* In: Osteoporosis, 202–226 (1994).

(List continued on next page.)

Primary Examiner—Patrick J. Nolan
(74) Attorney, Agent, or Firm—Sherry M. Knowles, Esq.; Stephanie D. Adams; King & Spalding LLP

(57) ABSTRACT

The present invention demonstrates that glucocorticoid-induced bone disease is due to changes in the birth and death rate of bone cells using a murine model of glucocorticoid excess as well as bone biopsy specimens obtained from patients with glucocorticoid-induced osteoporosis. This invention demonstrates that glucocorticoid administration increases apoptosis of mature osteoblasts and osteocytes and decreases bone formation rate and bone mineral density accompanied by defective osteoblastogenesis and osteoclastogenesis in the bone marrow.

4 Claims, 5 Drawing Sheets

OTHER PUBLICATIONS

Frey, F.J., *Kinetics and Dynamics of Prednisolone*, Endocrine Reviews. 8:453–473 (1987).

Frost, H.M., *In Vivo Osteocyte Death*, The Journal of Bone and Joint Surgery. 42–A:1–8: 138–150 (1960).

Giuliani et al. "Bisphosphonates stimulate formation of osteoblast precursors and mineralized nodules in murine and human bone marrow cultures in vitro and promote early osteoblastogenesis in young and aged mice in vivo." Bone (1998) 22(5):455–461.

Hill et al. "Multiple extracellular signals promote osteoblast survival and apoptosis." Endocrinology (1997) 138(9):3849–3858.

Jilka et al. "Osteoblast programmed cell death (apoptosis): modulation by growth factors and cytokines." Journal of Bone and Mineral Research (1998) 13(5):793–802.

Jilka et al. "Dexamethasone Promotes Apoptosis of Osteoblast Progenitors in Murine Bone Marrow Cultures: Antagonism by IL–6 Type Cytokines" Journal of Bone and Mineral Research (1997) 12(Supp): S455, abstract No. S411.

Manolagas et al. "New Developments in the pathagenesis and treatment of steroid–induced osteoporosis." Journal of Bone and Mineral Research (1999) 14(7):1061–1066.

Rogers et al. "Bisphosphonates induce apoptosis in mouse macrophage–like cells in vitro by a nitric oxide–independent mechanism." Journal of Bone and Mineral Research (1996) 11(10):1482–1491.

Tomkinson et al. "The role of estrogen in the control of rat osteocyte apoptosis." Journal of Bone and Mineral Research (1998) 13(8):1243–1250.

Aarden, E.M. et al. "Function of Osteocytes in Bone" J. Cell. Biochem. 55:287–299 (1994).

Bellido et. al. "PTH Prevents Glucocorticoid Apoptosis of Osteoblasts and Osteocytes In Vitro: Direct Interference with a private Death Pathway Upstrean of Caspase–3," Abstract. Bone. 23: S324 (1998).

Dunstan et al. "Osteocyte Death and Hip Fracture." Calcif Tissue Int 53: Suppll: S113–S117 (1993).

Falcini, F. et al., "Intravenous Administration of Alendronate Counteracts the In Vivo Effects of Glucocorticoids on Bone Remodeling, Calcified Tissue International." 58:166–169 (1996).

Felson and Anderson "Across–Study Evaluation of Association between Steroid Dose and Bolus Steroids and Avascular Necrosis of Bone." The Lancet Apr. 18: 902–905 (1987).

Jilka, R.L. et al., "Linkage of Decreased Bone Mass with Impaired Osteoblastogenesis in a Murine Model of Accelerated Senescence", The Journal of Clinical Investigation. 97:1732–1740 (1996).

Kato, Y., et al., "Establishment of an Osteocyte– like Cell Line, MLO–Y4." J. Bone Miser. Res., 12:2014–2023 (1997).

Manolagas et al. "Interleukin–6–type Cytokines and their Receptors" In Principles of Bone Biology. JP Bilezikian, LG Raisz, and GA Rodan, Editors, Academic Press, San Deiego, CA: 701–713 (1996).

Noble et al. "Identification of Apoptotic Changes in Osteocytes in Normal and Pathologic Human Bone" Bone 20:273–282 (1997).

Reid, I.R. et al., "Prevention of Glucocorticoid–Induced Osteoporosis." Journal of Bone and Mineral Research. 5::619–623 (1990).

Schwartz, B.D., et al., "Differential Regulation of Prostaglandin $E_2$ Synthesis and Phospholipase $A_2$ Activity by 1,25–$(OH)_2D_3$ in Three Osteoblast– like cell lines" Bone, (1992), 13: 51–58.

Weinstein, R.S. et al., "Inhibition of Osteoblastogenesis and Promotion of Apoptosis of Osteoblasts and Osteocytes by Glucocorticoids", The Journal of Clinical Investigation. 102:274–282 (1998).

Weinstein, S. et al., "Anatomic Juxtaposition of Apoptotic Osteocytes and Avascular Necrosis in Femurs from Patients with Glucocorticoid Excess", Bone. 23:S461 (1998).

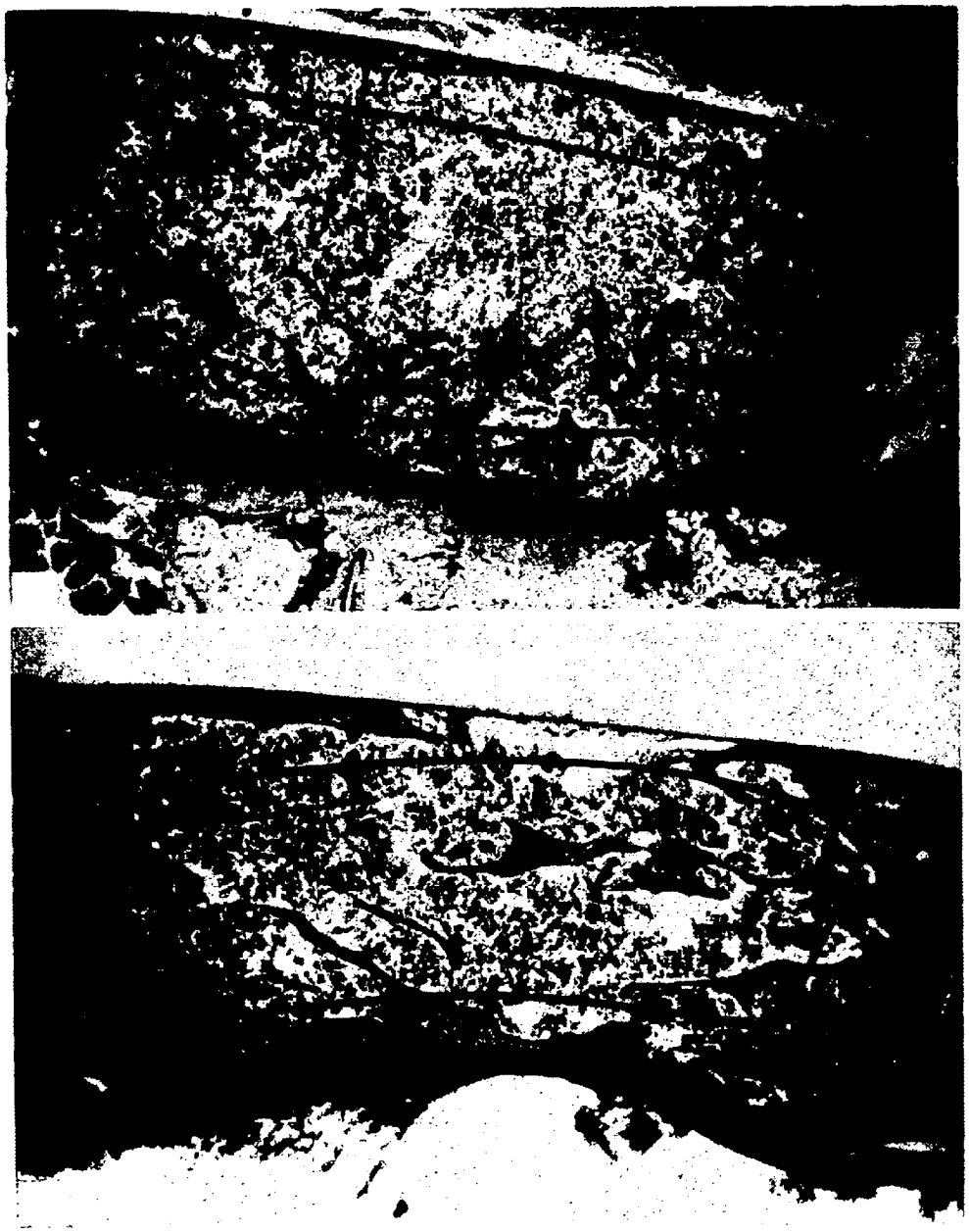

FIG. 3A
FIG. 3B

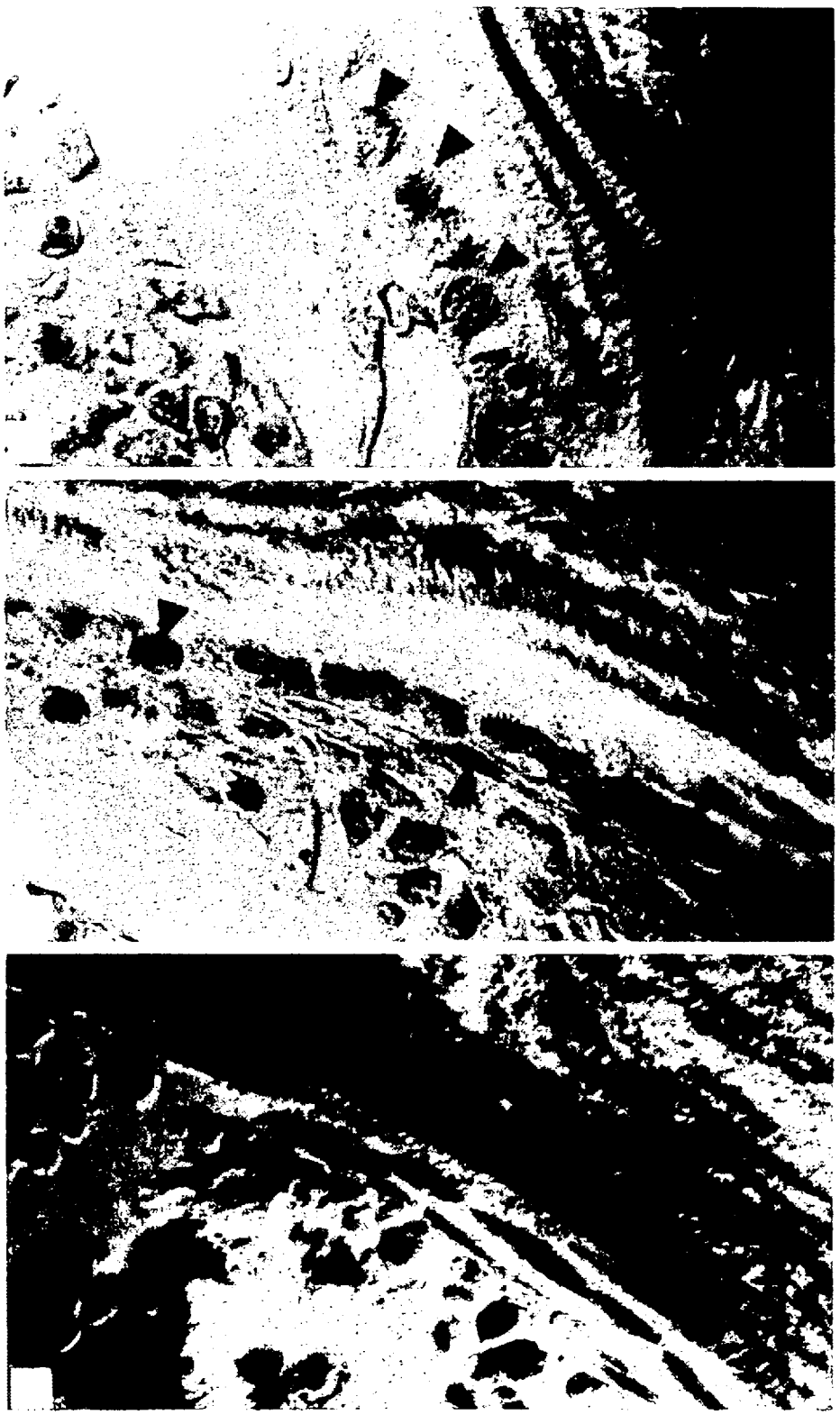

VITRO AND IN VIVO MODELS FOR SCREENING COMPOUNDS TO PREVENT GLUCOCORTICOID-INDUCED BONE DESTRUCTION

CROSS-REFERENCE TO RELATED APPLICATION

This application claims benefit of U.S. provisional application No. 60/105,805, filed Oct. 27, 1998, now abandoned.

BACKGROUND OF THE INVENTION

1. Field of the Invention

The present invention relates generally to bone physiology. More specifically, the present invention relates to in vitro and in vivo models for screening compounds to prevent glucocorticoid-induced bone destruction.

2. Description of the Related Art

The adverse effects of hypercortisolism on bone have been recognized for over 60 years (1), but the precise cellular and molecular basis of these changes has remained elusive. Today, the iatrogenic form of the disease has become far more common than Cushing's syndrome and glucocorticoid-induced osteoporosis is now third in frequency following post-menopausal and senile osteoporosis (2).

Bone loss due to glucocorticoid excess is diffuse, affecting both cortical and cancellous bone, but has a predilection for the axial skeleton. Spontaneous fractures of the vertebrae or ribs are, therefore, often presenting manifestations of the disorder (3,4). A cardinal feature of glucocorticoid-induced osteoporosis is decreased bone formation (5). In addition, patients receiving long-term glucocorticoid therapy sometimes develop collapse of the femoral head (osteonecrosis), but the mechanism underlying this is uncertain (6). Decreased bone formation, and in situ death of isolated segments of the proximal femur suggest that glucocorticoid excess may alter the birth and death of bone cells. Defective osteoblastogenesis has been reported to be linked to reduced bone formation and age-related osteopenia in the SAMP6 mouse (7). Besides the relationship between aberrant osteoblast production and osteoporosis, it has been recently shown that a significant proportion of osteoblasts undergo apoptosis (8), which raises the possibility that the premature or more frequent occurrence of osteoblast apoptosis could contribute to incomplete repair of resorption cavities and loss of bone.

Thus, the prior art is deficient in compounds that possess the advantageous properties of glucocorticoids, namely anti-inflammatory properties, but do not cause bone loss or osteoporosis. The present invention provides for methods of screening compounds to fulfill this long-standing need and desire in the art.

SUMMARY OF THE INVENTION

To demonstrate that glucocorticoid-induced bone disease is due to changes in the birth or death rate of bone cells, a murine model of glucocorticoid excess was used as well as bone biopsy specimens obtained from patients with glucocorticoid-induced osteoporosis. This invention demonstrates that glucocorticoid administration decreases bone formation rate and bone mineral density accompanied by defective osteoblastogenesis and osteoclastogenesis in the bone marrow and increases apoptosis of mature osteoblasts and osteocytes.

One object of the present invention is to provide methods to screen compounds that retain the anti-inflammatory properties of glucocorticoids yet do not result in bone loss or osteoporosis due to apoptosis of osteoblasts and osteocytes.

In one embodiment of the present invention, there is provided a method of screening for compounds that reduce the bone deteriorating effects of glucocorticoids, comprising the steps of: (a) contacting osteoblast and osteocyte cells with either a glucocorticoid alone or a glucocorticoid in combination with a test compound; and (b) comparing the number of cells undergoing apoptosis following treatment with the glucocorticoid alone or following treatment with the glucocorticoid in combination with the test compound; wherein a lower number of apoptotic cells following treatment with the glucocorticoid in combination with the test compound than with the glucocorticoid alone indicates that the test compound reduces the bone deteriorating effects of the glucocorticoid. This embodiment also includes the aforementioned method, wherein the compound has little effect on the anti-inflammatory properties of the glucocorticoid, further comprising the step of comparing the anti-inflammatory response of the glucocorticoid in combination with the test compound to the anti-inflammatory response of the glucocorticoid alone; wherein essentially equivalent anti-inflammatory responses of the glucocorticoid alone and the glucocorticoid in combination with the test compound is indicates that the test compound both reduces the bone deteriorating effects, while retaining the anti-inflammatory properties of the glucocorticoid; wherein said anti-inflammatory response is determined by models of inflammation selected from the group consisting of the adjuvant-induced arthritis model and hindlimb inflammation model.

In another embodiment of the present invention, there is provided a method of screening for glucocorticoid analogs that possess decreased apoptotic properties towards osteoblast and osteocyte cells, comprising the steps of: (a) contacting the cells with either a glucocorticoid or a glucocorticoid analog; and (b) comparing the number of apoptotic cells following treatment with the glucocorticoid or the glucocorticoid analog, wherein a lower number of apoptotic cells following treatment with the glucocorticoid analog than with the glucocorticoid indicates that the glucocorticoid analog possesses decreased apoptotic properties towards the cells. This embodiment also includes the aforementioned method, wherein the glucocorticoid analog retains anti-inflammatory properties, further comprising the step of: (c) comparing the anti-inflammatory response of the glucocorticoid in combination with a test compound to the anti-inflammatory response of the glucocorticoid alone, wherein essentially equivalent anti-inflammatory responses of the glucocorticoid alone and the glucocorticoid in combination with the test compound is indicative of a glucocorticoid analog that possesses decreased apoptotic properties while retaining anti-inflammatory properties; wherein said anti-inflammatory response is determined by models of inflammation selected from the group consisting of the adjuvant-induced arthritis model and hindlimb inflammation model.

In yet another embodiment of the present invention, there is provided a method of screening for compounds that stimulate bone development, comprising the steps of: (a) contacting osteoblast and osteocyte cells with either a glucocorticoid or a test compound; and (b) comparing the number of cells undergoing apoptosis following treatment with the glucocorticoid or the test compound; wherein a lower number of apoptotic cells following treatment with the test compound than with the glucocorticoid indicates that the test compound stimulates bone development.

In still yet another embodiment of the present invention, there is provided a method of screening for compounds that increase bone mineral density, comprising the steps of: (a) contacting osteoblast and osteocyte cells with either a glucocorticoid or a test compound; and (b) comparing the number of cells undergoing apoptosis following treatment with the glucocorticoid and the test compound; wherein a lower number of apoptotic cells following treatment with the test compound than with the glucocorticoid is indicative of a compound that increases bone mineral density.

In the above-mentioned embodiments, contacting is selected from the group consisting of in vitro cell cultures and in vivo murine animal model and determination of apoptosis is selected from the group consisting of TUNEL, DNA fragmentation and immunohistochemical analysis.

Other and further aspects, features, and advantages of the present invention will be apparent, from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows photomicrographs of the effects of prednisolone on murine vertebral cancellous bone. In panel A, is a longitudinal, panoramic section from a mouse receiving placebo and in panel B, a section from a mouse receiving prednisone. The histomorphometric reading area is outlined. Toluidine blue stain, original magnification ×25.

FIG. 3 shows the effect of prednisolone on murine osteoblast apoptosis. Osteoblasts were counted in undecalcified sections of cancellous bone from the vertebral secondary spongiosa. In panel A, the placebo group is shown and in panel B, the higher dose prednisolone group. Apoptotic cells in this experiment were identified using TUNEL and morphometric features such as nuclear fragmentation and condensation of chromatin (arrows). Methyl green counterstain viewed with Nomarski differential interference microscopy, original magnification ×400.

FIG. 5 shows the effect of chronic prednisone treatment on apoptosis in human bone. TUNEL-positive osteoblasts (arrowheads) and osteocytes (arrows) were absent from normal subjects (FIG. 5A) but were clearly identified in patients with prednisone-induced osteoporosis (FIG. 5B and FIG. 5C). Approximately 5% of the osteocytes and 30% of the osteoblasts were apoptotic. The photomicrographs are from transiliac bone biopsy specimens. Methyl green counterstain viewed with Nomarski differential interference microscopy, original magnification ×630.

DETAILED DESCRIPTION OF THE INVENTION

Figure 2A:
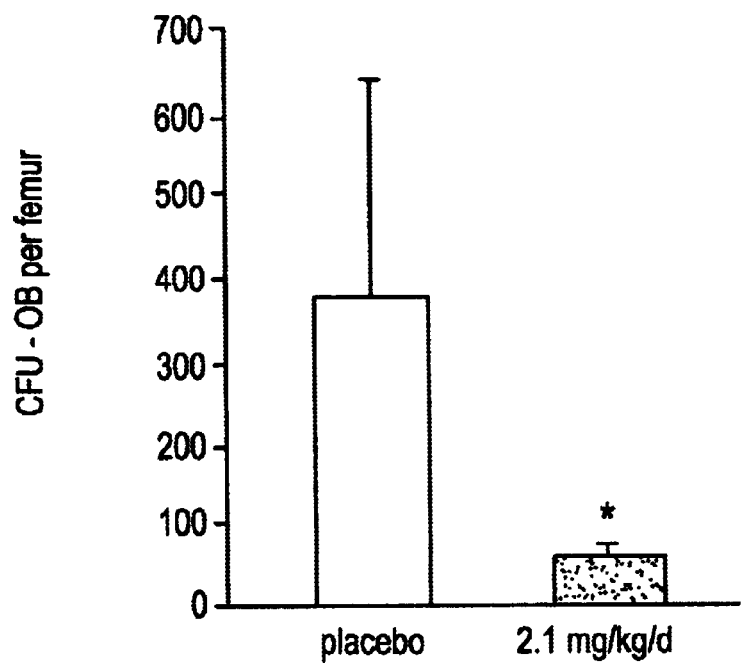
FIG. 2 shows quantification of CFU-OB and osteoclast progenitors formed in ex vivo bone marrow cell cultures. Marrow cells were obtained from the femurs of male mice after 27 d of exposure to placebo (white bars) or 2.1 mg/kg/d of prednisolone (black bars). Cells from each mouse were cultured separately.

Glucocorticoid-induced bone disease is characterized by decreased bone formation and in situ death of isolated segments of bone (osteonecrosis) suggesting that glucocorticoid excess, the third most common cause of osteoporosis, may affect the birth or death rate of bone cells thus reducing their numbers. To examine this, prednisolone was administered to 7-month-old mice for 27 days and decreased bone density, serum osteocalcin and cancellous bone area along with trabecular narrowing were found. These changes were accompanied by diminished bone formation and turnover, as determined by histomorphometric analysis of tetracycline-labeled vertebrae, and impaired osteoblastogenesis and osteoclastogenesis, as determined by ex vivo bone marrow cell cultures. In addition, the mice exhibited a 3-fold increase in osteoblast apoptosis in vertebrae and showed apoptosis in 28% of the osteocytes in metaphyseal cortical bone. As in mice, an increase in osteoblast and osteocyte apoptosis was documented in patients with glucocorticoid-induced osteoporosis. Decreased production of osteoclasts explains the reduction in bone turnover while decreased production and apoptosis of osteoblasts would account for the decline in bone formation and trabecular width. Furthermore, accumulation of apoptotic osteocytes may contribute to osteonecrosis. These findings provide evidence that glucocorticoid-induced bone disease arises from changes in the numbers of bone cells.

The present invention is directed towards methods of screening compounds that retain the anti-inflammatory properties of glucocorticoids while lacking the bone degeneration properties associated with long-term administration due to apoptosis of osteoblasts and osteocytes.

The present invention is further directed towards methods of screening compounds that promote bone regeneration by inhibiting the apoptosis of osteoblasts and osteocytes.

As used herein, the terms "glucocorticoid" and "glucocorticoid analog" is defined as substances that bind to the glucocorticoid receptor.

As used herein, the term "apoptosis" refers to programmed cell death with nuclear fragmentation and cell shrinkage as detected by morphological criteria and Terminal Uridine Deoxynucleotidal Transferase Nick End Labeling (TUNEL) staining.

As used herein, the terms "anti-inflammatory response" or "anti-inflammatory property" refers to preventing the induction of cytokines and other events that lead to T cell activation. Several models of inflammation are routinely used in the art, including the adjuvant-induced arthritis model and hindlimb inflammation model which are well known to those having ordinary skill in this art (54, 55).

As used herein, the term "bone mineral density" refers to bone mass as defined by Dual-Energy X-Ray Absorbtiometry (DEXA).

The following examples are given for the purpose of illustrating various embodiments of the invention and are not meant to limit the present invention in any fashion:

EXAMPLE 1

Animals

Male Swiss Webster mice (Charles River Laboratories, Stone Ridge, N.Y.) were electronically tagged (Biomedic Data System Inc., Maywood, N.J.) and kept in plastic cages (3–5 animals per cage) under standard laboratory conditions with a 12 hr dark, 12 hr light cycle and a constant temperature of 20° C. and humidity of 48%. All mice were fed on a standard rodent diet (Agway RMH 3000, Arlington Heights, Ill.) containing 22% protein, 5% fat, 5% fiber, 6% ash, 3.5 Kcal/g, 1.0 IU vitamin D3/g, 0.97% calcium and 0.85% phosphorus with water ad libitum. The animals and food supply were weighed at one week intervals throughout the experiment. Studies were approved by the UAMS Division of Laboratory and Animal Medicine.

EXAMPLE 2

Glucocorticoid Administration—experimental Design

Bone mineral density (BMD) determinations were done at two week intervals to identify the peak adult bone mass of the mice, which was reached between 5 and 6 months-of-age (9). Animals at peak bone mass were used to avoid obscuring the negative impact of glucocorticoid excess on bone mineral density by the confounding effects of increased linear and radial growth. Before the experiment began, bone mineral density measurements were repeated to allocate the animals into groups (n=4–5) with equivalent spinal density values. The mice (7-mo-old) received placebo or prednisolone, a synthetic glucocorticoid analog that does not require hepatic hydroxylation and has minimal mineralocorticoid activity, thus eliminating the need for potassium supplementation or sodium restriction (10,11). Implantation of pellets releasing 0.5 mg/kg/d of prednisolone (the no effect dose) did not decrease bone mineral density. Therefore, two doses were used, 0.7 mg/kg/d (lower dose) and 2.1 mg/kg/d (higher dose), chosen from pilot studies to bracket the dose (1.4 mg/kg/d) that invariably causes densitometric evidence of bone loss. These doses were administered for 27 days by subcutaneous implantation of slow-release pellets (Innovative Research of America, Sarasota, Fla.). Bone mineral density measurements were obtained at the beginning of the experiment and 27 days post-implantation. For dynamic histomorphometric measurements, tetracycline HCl (30 mg/kg body weight) was given intraperitoneally 17 and 23 days post-implantation. After 27 days, the mice were sacrificed, serum and urine specimens were taken, bone marrow aspirates were obtained from the right femur for ex vivo marrow cell cultures and the left femur and lumbar vertebrae were prepared for histomorphometric analysis. Livers were examined for fatty infiltration as a sign of prednisolone toxicity. The weight of the seminal vesicles (mg/100 g body weight) was used as an index of the androgen status of the animals (12). To help interpret these measurements, a separate group of animals was orchidectomized (n=5).

EXAMPLE 3

Bone Densitometry

Dual-energy X-ray absorptiometry (DEXA) was used to determine global (whole body minus the head), spinal and hindquarters bone mineral density in live mice (7,9). The scans done at 27 days after pellet implantation were analyzed using the 'Compare' technique, in which the evaluation is based on the exact positioning and region of interest placement of the baseline scan. Accuracy of the DEXA measurements was demonstrated by the strong linear relationship between ash weight and bone mineral content at each region (7). Over the 18 months, the coefficient of variation for the bone mineral density of a plastic-embedded whole mouse skeleton was 3.0% (n=146).

EXAMPLE 4

Serum and Urine Biochemical Measurements

Serum osteocalcin was measured by radioimmunoassay using a goat anti-murine osteocalcin and murine osteocalcin as tracer and standard (Biomedical Technologies, Stoughton, Mass.). Urinary free deoxypyridinoline excretion was determined by a microtiter competitive enzyme immunoassay (Pyrilinks-D, Metra Biosystems, Mountain View, Calif.) and was expressed as a ratio to the urinary creatinine.

EXAMPLE 5

Bone Histomorphometric Analysis

The distal femora and lumbar vertebrae were fixed in 4° C. Millonig's phosphate-buffered 10% formalin, pH 7.4, embedded undecalcified in methyl methacrylate and stained (7,9,13). The histomorphometric examination was done with a computer and digitizer tablet (OsteoMetrics Inc. Version 3.00, Atlanta, Ga.) interfaced to a Zeiss Axioscope (Carl Zeiss, Inc., Thornwood, N.Y.) with a drawing tube attachment. All cancellous measurements were two-dimensional, confined to the secondary spongiosa and made at ×400 magnification (numerical aperture 0.75). The terminology and units used are those recommended by the Histomorphometry Nomenclature Committee of the American Society for Bone and Mineral Research (14). The trabecular width and osteoid width were measured directly. Trabecular spacing and number were calculated (15). Only TRAPase-positive cells were included in the osteoclast perimeter. The rate of bone formation ($\mu m^2/\mu m/d$) and turnover (%/d) were calculated (7).

EXAMPLE 6

Detection and Quantification of Osteoblasts and Osteoclasts in ex vivo Bone Marrow Cultures One femur from each mouse was flushed with 5 ml of phenol red-free αMEM (Gibco BRL, Gaithersburg, Md.) containing 10% FBS (Hyclone, Logan, Utah) to obtain marrow cells. After the cells were rinsed and resuspended to obtain a single cell suspension, the nucleated cell count was determined using a Coulter Counter. Cells from each animal were cultured separately.

The number of colony-forming unit-fibroblast (CFU-F) and CFU-osteoblast (CFU-OB) present in the bone marrow preparations were determined (16–18). Briefly, cells were seeded at $1.5 \times 10^6$ per 10 $cm^2$ well for the determination of CFU-F number and maintained for 10 days in phenol red-free αMEM containing 15% preselected FBS, 50 $\mu M$ ascorbic acid and 10 mM β-glycerophosphate (Sigma Chemical Co, St. Louis, Mo.) with one-half of the medium replaced after 5 days. After fixation in neutral buffered formalin and staining with hematoxylin, colonies containing a minimum of 20 fibroblastoid cells were enumerated. Cells were seeded at $2.5 \times 10^6$ cells per 10 $cm^2$ well for the determination of CFU-OB number and cultured for 25–28 days as described above for CFU-F. After fixation in 50% ethanol and 18% formaldehyde, cultures were stained using Von Kossa's method to visualize and enumerate colonies containing mineralized bone matrix.

Osteoclast formation in bone marrow cultures was assessed in replicate cultures (4–6 from each animal) maintained for 9 days in the presence of αMEM, 10% FBS and 10 nM 1.25(OH)$_2$D$_3$ (7). Briefly, marrow cells were cultured at 1.5×10$^6$ per 2 cm$^2$ well on 13 mm round Thermanox disks and maintained for 8 days in the presence of 10% FBS in αMEM supplemented with 10$^{-8}$ M 1.25(OH)$_2$D$_3$ (provided by Dr. Milan Uskokovic, Hoffman-LaRoche, Nutley, N.J.). At the end of the experiment, cells were processed for the autoradiographic detection of bound $^{125}$I-calcitonin ($^{125}$I-CT) and stained for tartrate-resistant acid phosphatase. Because many osteoclasts in murine bone possess only one nucleus (7), it is impossible to distinguish between preosteoclasts and mononuclear osteoclasts in ex vivo cultures of murine bone marrow cells. Therefore, mononucleated and multinucleated cells that both bind $^{125}$I-CT and express TRAPase were designated as osteoclastic cells. The number of osteoclasts formed in this assay is a reflection of the number of osteoclast progenitors present in the bone marrow aspirate and the number of stromal/osteoblastic support cells that form during the culture period.

The number of CFU-F colonies, CFU-OB colonies, and osteoclastic cells formed from the marrow cells of each animal was expressed as the number per femur, which was calculated by multiplying the number of colonies or osteoclasts obtained per 10$^6$ cells seeded at the initiation of the cultures by the total number of marrow cells obtained from the animal.

EXAMPLE 7

Measurement of Apoptosis in Undecalcified Bone Sections

Sections were mounted on silane-coated glass slides (Scientific Device Lab, Inc., Des Plains, Ill.), deplasticized and incubated in 10 mM citrate buffer, pH 7.6, in a microwave oven at 98° C. for 5 minutes. Slides were then incubated with 0.5% pepsin for 30 minutes at 37° C. Apoptotic cells were detected by the TUNEL reaction (transferase-mediated biotin-dUTP nick end-labeling) using Klenow terminal deoxynucleotidyl transferase (Oncor, Gaithersburg, Md.) in sections counterstained with 1% methyl green. The TUNEL reaction was noted within cell nuclei and the cells whose nuclei were clearly brown from the peroxidase-labeled anti-digoxigenin antibody instead of the blue-green from the methyl green were interpreted as positive. Plastic-embedded sections of weaned rat mammary tissue were used as a positive control. Negative controls were made by omitting the transferase. Morphological changes characteristic of apoptosis were examined carefully to minimize ambiguity regarding the interpretation of results. With these precautions, TUNEL has been unequivocally associated with apoptosis (19). In addition, TUNEL has been used with DNA fragmentation and immunohistochemical studies to demonstrate apoptosis of osteoblastic cells and osteoblasts both in vitro and in vivo (8,20). Apoptosis was also assessed in transiliac bone biopsy specimens taken from two patients with glucocorticoid-induced osteoporosis (22- and 36-yr-old, receiving 15 to 25 mg/d of prednisone for 3 to 6 yr) and from 12 age-, sex- and race-matched controls (13). Two longitudinal sections were examined from each patient and control subject. Osteoblasts were identified as cuboidal cells lining the osteoid-covered trabecular perimeter (7,9,13). Osteocytes were identified inside lacunae in mineralized bone.

EXAMPLE 8

Statistics

Differences in the bone densitometry values were determined using the percentage change in BMD from baseline. Dose response relations were tested by one-way ANOVA. To further evaluate changes in bone histomorphometry, a Student's t test was used to assess for significant differences between group means, after testing for equivalence of variances and normal distribution of data. The significance of the relative frequency of apoptotic cells was determined with the $\chi^2$ statistic. P values less than 0.05 were considered significant (21).

EXAMPLE 9

Demonstration of Bone Loss in Mice Receiving Prednisolone

In mice implanted with the higher dose of prednisolone, global and spinal BMD at 27 days were significantly lower than those found in the mice that were implanted with placebo pellets (TABLE I). The decrease in global bone mineral density was dose dependent (P<0.05). Demonstrating the expected propensity for the axial skeleton, glucocorticoid-induced loss of bone mineral density was less conspicuous at the hindquarters. The levels of serum osteocalcin, a marker of osteoblast activity, were decreased more than 50% when compared to placebo, while urinary deoxypyridinoline excretion was not significantly different between the groups (TABLE I). These effects were not due to changes in food intake, body weight or androgen status (TABLE II). In addition, hepatic fatty infiltration was absent.

TABLE I

Bone Mineral Density (BMD) and Serum and Urine Biochemical Measurements in Prednisolone-treated Mice

| Measurement | Placebo | 0.7 mg/kg/d | 2.1 mg/kg/d |
| --- | --- | --- | --- |
| Global BMD (% change) | −2.7 ± 2.1 | −5.0 ± 2.2* | −6.6 ± 1.9† |
| Spinal BMD (% change) | −3.1 ± 3.0 | −6.8 ± 3.2 | −8.7 ± 3.5* |
| Hindquarters BMD (% change) | 0.4 ± 10.4 | −3.8 ± 8.0 | −3.4 ± 6.9 |
| Osteocalcin (µg/L) | 93.8 ± 11.5 | 63.0 ± 27.7* | 46.4 ± 13.8† |
| Deoxypyridinoline (µM/mM creatinine) | 78.3 ± 9.3 | 63.6 ± 14.7 | 81.5 ± 11.3 |

Data shown are the mean ± SD from 5–7 animals. *P < 0.05 vs placebo; †P < 0.005 vs placebo.

TABLE II

Food Intake, Body Weight and Seminal Vesicle Weight in Prednisolone-treated Mice

| Measurement | Placebo | 0.7 mg/kg/d | 2.1 mg/kg/d |
| --- | --- | --- | --- |
| Food Intake (g/d) | 3.4 ± 0.6 | 3.6 ± 0.2 | 3.7 ± 0.4 |
| Body Weight (g) | 37.9 ± 6.0 | 33.8 ± 4.3 | 32.2 ± 4.2 |
| Seminal Vesicle Weight (mg/100 g body weight) | 74.6 ± 14.6 | 92.7 ± 8.7 | 83.1 ± 6.9 |

Data = mean ± SD. Seminal vesicle weight in a orchidectomized control was 11.3 ± 3.1 mg/100 g body weight, P < 0.001 vs treated mice.)

EXAMPLE 10

Effects of Glucocorticoid Administration on Vertebral Bone Histomorphometry

Consistent with the bone mineral density results, in the animals receiving the higher dose, there was a 40% decline in the vertebral cancellous bone area and a 23% decline in trabecular width (P<0.01) (TABLE III). In both prednisolone groups, there was a trend towards increased trabecular spacing and there was decreased trabecular number in the lower dose group indicating that some trabecular profiles were entirely resorbed.

In the higher dose group, osteoid area decreased by 29%, osteoid perimeter by 34% and osteoid width by 27% ($P<0.01$). A trend toward decreased osteoblast and osteoclast perimeters was found in the animals receiving the higher dose. There was, however, a 3-fold increase in the empty erosion cavities (devoid of osteoclasts) or reversal perimeter. The tetracycline-based histomorphometry showed that prednisolone administration caused a 26% decrease in the mineralizing perimeter ($P<0.05$). In addition, a dose-dependent decrease in the mineral appositional rate was noted ($P<0.05$); this decline was 22% with the lower dose and 40% with the higher dose. Furthermore, there was a 53% decrease in the rate of bone formation with the higher dose ($P<0.01$), which correlated with the vertebral cancellous bone area ($r=0.57$, $P<0.05$), indicating that the glucocorticoid-induced decreases in bone area were associated with a reduction in the rate of bone formation. Bone turnover, expressed as a percentage of the bone area per day, also decreased in a dose-dependent manner ($P<0.05$).

TABLE III

Vertebral Cancellous Bone Histomorphometry in Swiss Webster Mice After 27 Days of Prednisolone Administration

| Histomorphometric Determination | Placebo | 0.7 mg/kg/d | 2.1 mg/kg/d |
|---|---|---|---|
| Bone area/Tissue area(%) | 10.4 ± 1.4 | 6.9 ± 2.1 | 6.3 ± 1.7† |
| Trabecular width ($\mu$m) | 48.0 ± 2.4 | 48.6 ± 4.3 | 37.1 ± 4.4† |
| Trabecular spacing ($\mu$m) | 423 ± 69 | 712 ± 302 | 546 ± 125 |
| Trabecular number (per mm) | 1.66 ± 0.6 | 1.44 ± 0.47 | 1.77 ± 0.33 |
| Osteoid area/Bone area (%) | 2.1 ± 0.2 | 2.2 ± 0.8 | 1.5 ± 0.2† |
| Osteoid perimeter/Bone perimeter (%) | 15.1 ± 2.1 | 15.8 ± 5.1 | 9.9 ± 1.1† |
| Osteoid width ($\mu$m) | 2.6 ± 0.4 | 2.0 ± 0.3 | 1.9 ± 0.3* |
| Osteoblast perimeter/Bone perimeter (%) | 1.2 ± 0.9 | 2.2 ± 0.2 | 0.5 ± 0.4 |
| Osteoclast perimeter/Bone perimeter (%) | 2.7 ± 1.1 | 2.6 ± 0.5 | 1.1 ± 1.7 |
| Reversal perimeter/Bone perimeter | 2.5 ± 2.3 | 3.2 ± 2.2 | 7.2 ± 1.1† |
| Mineralizing perimeter/Bone perimeter (%) | 12.9 ± 0.5 | 13.9 ± 5.6 | 9.5 ± 2.5* |
| Mineral appositional rate ($\mu$m/d) | 1.23 ± 0.11 | 0.96 ± 0.11* | 0.74 ± 0.20† |
| Bone formation rate/Bone perimeter ($\mu$m2/(m/d) | 0.15 ± 0.02 | 0.13 ± 0.04 | 0.07 ± 0.03† |
| Bone turnover (%/d) | 0.68 ± 0.09 | 0.46 ± 0.12* | 0.24 ± 0.11† |

Data shown are the mean ± SD. There are 4–5 animals per group. *$P < 0.05$ vs. placebo; †$P < 0.01$ vs. placebo.

EXAMPLE 11

Figure 2B:
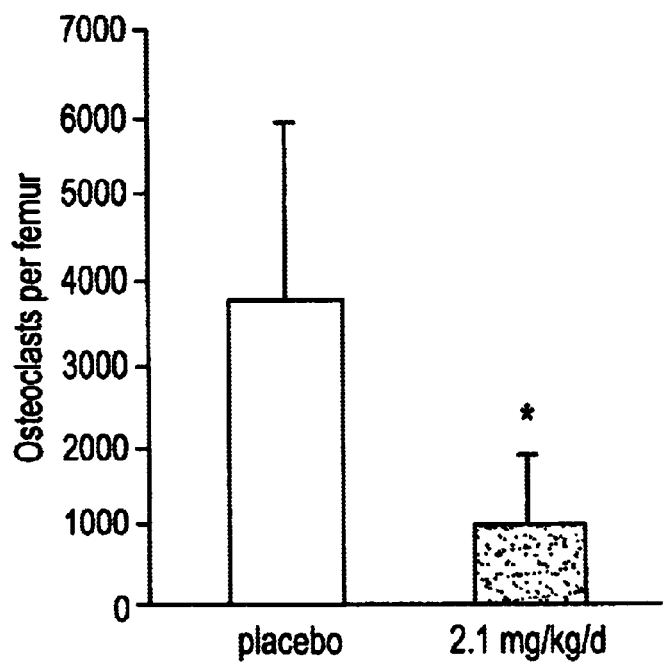

Effects of Glucocorticoid Administration on Osteoblastogenesis and Osteoclastogenesis In bone marrow cell cultures from the animals receiving the higher dose, there was no significant change in CFU-F colonies (1250±374 vs. 698±104, NS). However, the number of CFU-OB colonies decreased by 86% (375±257 SD vs. 54±14, $P<0.05$) and the number of osteoclastic cells formed in response to $1.25(OH)_2D_3$ in ex vivo marrow cultures decreased by 65% (1387±920 vs. 492±311, $P<0.05$) (FIG. 2).

EXAMPLE 12

Effects of Glucocorticoid Administration on Apoptosis

Counting a total of 973 osteoblasts, there was a 3-fold increase in osteoblast apoptosis in the vertebral cancellous bone of mice receiving the higher dose of prednisolone when compared to controls (2.03%±0.34 vs. 0.66%±0.07, $P<0.05$). Morphological changes typical of apoptosis accompanied the TUNEL-positive osteoblasts and included sharply defined, condensed chromatin plastered against the nuclear membrane, nuclear fragmentation and cell shrinkage (FIGS. 3A and 3B).

Figure 4A:
FIG. 4 shows the effect of prednisolone on murine osteocyte apoptosis. The cells were counted in undecalcified sections of femoral metaphyseal cortical bone. In panel A, the placebo group is shown and in panel B, the higher dose prednisolone group. Apoptotic osteocytes (arrowheads) are seen in close proximity to normal cells. Methyl green counterstain viewed with Nomarski differential interference microscopy, original magnification ×630.
Figure 4B:

In addition, prednisolone caused the appearance of apoptotic osteocytes in cortical bone sections taken from femora (FIGS. 4A and 4B). Whereas none of the osteocytes exhibited apoptotic features in the control animals, 28% of 131 cortical osteocytes were apoptotic in the animals receiving the higher dose. Osteocyte apoptosis was restricted to small groups of cells in the center of the femoral metaphyseal cortex and were absent from vertebral cortical bone. The apoptotic osteocytes were identified in close proximity to normal osteocytes, in contrast to the large homogenous areas of dead and dying cells typical of cell necrosis. An increase in apoptotic hypertrophic chondrocytes and bone marrow cells was also noted in mice receiving either dose of prednisolone. Osteoclast apoptosis was not observed.

EXAMPLE 13

Demonstration of Apoptotic Osteoblasts and Osteocytes in Patients With Glucocorticoid-induced Osteoporosis In transiliac bone biopsies taken from two patients, TUNEL-positive osteoblasts and osteocytes were clearly identified in both (FIG. 5B and 5C) but were absent from specimens taken from 12 age-, sex- and race-matched controls (FIG. 5A). As in the murine model, bone histomorphometry from these two patients showed the changes expected with chronic glucocorticoid therapy (5): reduced cancellous bone area (11.1 and 8.8%, normal is 22.4±1.2 SEM), decreased trabecular width (62 and 118 $\mu$m, normal is 161±9), decreased osteoblast perimeter (2.1=and 2.3%, normal is 7.6±0.4), decreased osteoclast perimeter (0 and 0.4%, normal is 0.9±0.2), increased reversal perimeter (13.5 and 15.4%, normal is 6.9±0.7) and diminished bone formation rate (0.02 and 0.05 $\mu m^2/\mu m/d$, normal is 0.095±0.012). In the cancellous bone of these specimens, approximately 5% of the osteocytes and 30% of the osteoblasts were apoptotic. Apoptosis of osteoclasts or cortical osteocytes was not observed. A transiliac bone biopsy represents a much smaller sample of the human skeleton than the murine femur and lumbar vertebrae represent of the mouse skeleton. Therefore, it is not surprising that the percentage of apoptotic osteoblasts and osteoclasts was different in the human and murine specimens.

EXAMPLE 14

Early Effects on Bone Resorption

To directly establish whether glucocorticoids initially accelerate bone resorption in the mouse, the vertebral cancellous bone histology were examined in an additional group of somewhat younger mice (5-mo-old) after 7 days administration of the higher dose of prednisolone or placebo (n=5). It was found that whereas prednisolone caused a 59% decrease in the osteoblast perimeter (5.2%±1.5 SD vs. 2.1±1.1, $P<0.005$), the osteoclast perimeter increased 96% (0.51%±0.34 vs. 1.00±0.41, $P<0.05$).

Summary

The choice of the mouse for these studies was based on its validity as a model of the bone loss associated with loss of sex steroids (9,22) and with senescence (7), but the mouse also has several advantages over other animals (TABLE IV). In the mouse, glucocorticoid administration consistently induces axial, greater than appendicular, bone loss without weight loss or hypogonadism, accompanied by histological indices of impaired osteoblast function, thus reproducing the major features of the human disease (2–5). Although the doses used in the studies described herein were higher in relation to body weight than in humans, they were only mildly higher than the dose determined by serial bone densitometry to have no effect and were consistent with the much higher metabolic clearance of glucocorticoids and other compounds in laboratory animals than in humans (35–37). Nonetheless, the similarity of the glucocorticoid-induced increases in apoptotic cells and bone histomorphometric features in mice and humans indicates that the observations in the mouse are not due to pharmacological differences.

The effects of glucocorticoids were examined after 27 days, a period equivalent in the mouse to about 3 to 4 years in humans. Thus, these findings represent long-term, rather than acute effects. Although a significant correlation was found between the severity of the cancellous bone loss and the extent of reduction in bone formation, several other lines of evidence imply that some of the observed bone loss was due to an early increase in bone resorption which had subsided by the time of examination. First, there was suggestive evidence of complete loss of some trabeculae (TABLE III). Second, based on the bone turnover measured in the placebo group which must be close to the rate found in all the animals at the beginning of the study, even with total suppression of bone formation, the initial rate of bone turnover could have accounted only for an exponential decline in cancellous bone area of 18%, whereas a 40% decrease was observed. Finally, an early increase in osteoclast perimeter was confirmed by histomorphometric examination of vertebral cancellous bone after 7 days of prednisolone administration.

By 27 days of prednisolone administration, bone resorption fell to, or below, normal, as indicated by the downward trend in the osteoclast perimeter, normal urinary deoxypyridinoline excretion and profound decrease in osteoclastogenesis. The persistent increase in erosion cavities devoid of osteoclasts, measured as the reversal perimeter, merely indicates delayed bone formation (38), and has been previously observed in glucocorticoid-treated patients (5,39). Consequently, the present invention emphasizes the relevant findings at 27 days to chronic, rather than short-term, glucocorticoid administration to humans.

Vertebral cancellous bone in adult mice undergoes sequential, coupled bone remodeling that is qualitatively similar to that occurring in human bone (7,9). Many of the changes in cellular, osteoid and tetracycline-based histological indices induced by glucocorticoid administration can be accounted for by a reduction in the activation frequency of bone remodeling, the main determinant of the rate of bone turnover (40), which is an inevitable consequence of the substantial decrease in osteoclastogenesis that was observed. Although a reduction in bone turnover will not by itself cause bone loss, the decrease in trabecular width, which was the major structural change observed, is usually the result of incomplete cavity repair. This is, at least in part, due to inadequate osteoblast recruitment, either from diminished production or ineffective migration to the bone surface (40). The reduction in osteoblastogenesis was of sufficient magnitude to explain the decrease in bone formation rate, and would also have contributed to the inadequate osteoblast recruitment and consequent decline in trabecular width. Thus, the inhibitory effect of glucocorticoids on early bone cell progenitors in the bone marrow can account for many of the in vivo observations.

The data herein also bear on recent ideas concerning the relationships between early osteoblast and osteoclast progenitors in the bone marrow. Although mature osteoclasts and osteoblasts are needed successively at each bone surface site that is being remodeled, these cells are needed simultaneously as the basic multicellular unit (which is the instrument of bone remodeling) progresses through or across the surface of bone (41). The necessary parallel production of executive cells is accomplished by signals that originate from early members of the stromal cell-osteoblast family, which support in various ways the production of mononuclear preosteoclasts in the bone marrow (42). The demonstration herein of a marked reduction in the numbers of both CFU-OB and osteoclast progenitors derived from ex vivo bone marrow cell cultures makes it likely that glucocorticoid administration inhibits the proliferation and/or differentiation of the stromal cell-osteoblast family at a n early stage, leading to a reduction in the number of mature, matrix-secreting osteoblasts as well as the osteoblastic cells that support osteoclast development. A direct inhibitory effect of glucocorticoids on osteoclast precursor proliferation is not excluded by the data herein, but would be less easy to reconcile with the finding of a n early increase in the osteoclast perimeter.

Some osteoblasts become osteocytes and some become lining cells, but these fates combined do not account for all the osteoblasts initially present. Although migration along or away from the bone surface is possible, death has always seemed the most likely alternative fate (43). Osteoblasts in remodeling bone undergo apoptosis with a frequency sufficient to account for most or all of those missing (8). Based on the dynamic histomorphometry at the murine vertebral secondary spongiosa and a wall width of about 15 μm (7,9,14), the mean active life span of an osteoblast was calculated on cancellous bone by dividing wall width by the mineral appositional rate. From this calculation, the mean active lifespan of a murine osteoblast is about 12 days or 288 hours. The prevalence of osteoblast apoptosis in the present study was 0.0066 in the placebo group. The following relationship was applied:

$$t_{Ap}/288 = 0.0066/f_{Ap},$$

where $t_{Ap}$ is the mean duration (in hours) of the DNA fragmentation phase of apoptosis that is detected by TUNEL, and $f_{Ap}$ is the fraction of osteoblasts that undergoes apoptosis and based on a value of $t_{Ap}$ of about 3 hours, determined previously for regenerating liver (44), the corresponding value for $f_{Ap}$ in the placebo group is 0.6. Thus, the low prevalence of apoptosis in the placebo group is consistent with studies of human bone that 50–70% of osteoblasts undergo apoptosis, and that only a minority become osteocytes or lining cells (43).

In the animals receiving the higher dose of prednisolone, the prevalence of apoptosis was 0.0203. With prednisolone administration, phagocytosis of the apoptotic cells would b e suppressed and it was estimated that $t_{Ap}$ could be doubled (45). Wall width was reduced to about 8 μm and mineral appositional rate to 0.74 μm/d, so that the active lifespan of an osteoblast is about 260 hours. In these circumstances, the corresponding value for $f_{Ap}$ in the prednisolone group is 0.9. Although there is some uncertainty to the assumptions used for these estimates, the approach does help explain the data and disclose the devastating impact of glucocorticoid excess on osteoblast survival. The higher proportion of osteoblasts showing features of apoptosis in glucocorticoid-treated mice and human subjects could indicate no more than prolongation of the time needed for completion of the process, but it is more likely that glucocorticoids induce apoptosis, either prematurely in cells already destined for this fate or in cells otherwise destined to become lining cells or osteocytes. In either case, the mean active lifespan of osteoblasts would be shortened and less bone formed. Thus, the reduction in bone formation by glucocorticoids could be due to increased death as well as decreased birth of osteoblasts.

Osteocytes are long-lived but not immortal cells. In human rib cortical bone, their lifespan has been estimated at about 20 years (47); if bone remains unremodeled for a longer time, the osteocytes die, as revealed by empty, lacunae and hypermineralized perilacunar bone, referred to as micropetrosis (48). Osteocyte death in cancellous bone, indicated by absence of lactic dehydrogenase activity, increases in prevalence with age in the upper femur but not in the vertebrae (49), probably because of the higher bone turnover in the spine. Empty lacunae and enzyme absence can reveal the fact, but not the mode, of death. Osteocyte apoptosis has recently been detected in human iliac cancellous bone and its prevalence was increased by pharmacological induction of estrogen deficiency (19). The present invention demonstrated that chronic glucocorticoid administration, both to mice and to human patients, likewise increases the prevalence of osteocyte apoptosis. The proportion of apoptotic osteocytes was much higher than of osteoblasts, reflecting the unique unavailability of osteocytes for phagocytosis because of their anatomic isolation from scavenger cells, and the need for extensive degradation to small molecules to dispose of the cells through the narrow canaliculi. As a result, the process is prolonged and affected cells accumulate.

The network of osteocytes probably participates in the detection of microdamage and the transmission of signals that lead to its repair by remodeling (50). Disruption of the network by osteocyte apoptosis could compromise this mechanism, leading to microdamage accumulation and increased bone fragility (51). Second, chronic glucocorticoid administration sometimes leads to so-called aseptic or avascular necrosis of bone (6). Glucocorticoid-induced osteocyte apoptosis, a cumulative and unrepairable defect, would explain the correlation between total dose and incidence of avascular necrosis of bone (53) and its occurrence after glucocorticoid administration had ceased.

In conclusion, the present invention has demonstrated that the mouse is a valid and informative model of glucocorticoid-induced bone disease, not confounded by weight loss or sex-steroid deficiency, and that many of the effects of chronic glucocorticoid administration on bone can be explained by decreased birth of osteoblast and osteoclast precursors and increased apoptosis of mature osteoblasts and osteocytes.

TABLE IV

Confounding Factors with Glucocorticoid Administration

| Animals | Factors |
|---|---|
| Rats (23,24) | Paradoxical increase in cancellous bone mass*, decreased food intake and weight. |
| Rabbits and dogs (25–27) | Inconsistent changes in bone density and cancellous bone area, weight loss, hepatic fatty infiltration. |
| Ewes (28–30) | Histological changes resemble glucocorticoid-treated patients but corresponding changes in bone density and cancellous bone area are inconsistent. |

*Glucocorticoids inhibit bone resorption and promote apoptosis in rat osteoclasts in vitro (31), whereas bone resorption is stimulated in neonatal mouse calvaria (32). Glucocorticoids stimulate bone nodule formation from rat calvarial cells in vitro (33) but inhibit differentiation in a murine osteoblastic cell line (34).

The following references were cited herein:
1. Cushing, H. 1932. Bull. Johns Hopkins Hosp. 50:137–195.
2. Lukert, B. 1996. Glucocorticoid-induced osteoporosis. In Osteoporosis. R. Marcus, D. Feldman, and J. Kelsey, editors. Academic Press, San Diego, Calif. 801–820.
3. Fitzpatrick, L. A. 1994. Glucocorticoid-induced osteoporosis. In Osteoporosis. R. Marcus, editor. Blackwell Scientific Publications, Boston, Mass. 202–226.
4. Reid, I. R. 1989. Clin. Endocrinol. 30:83–103.
5. Dempster, D. 1989. J. Bone Miner. Res. 4:137–141.
6. Mankin, H. J. 1992. N. Engl. J. Med. 326:1473–1479.
7. Jilka, R. L., et al. 1996. J. Clin. Invest. 97:1732–1740.
8. Jilka, R. L., et al. 1998. J. Bone Miner. Res. 13: (in press).
9. Weinstein, R. S., et al. 1997. Endocrinol. 138: 4013–4021.
10. Frey, F. J. 1987. Endo. Rev. 8:453–473.
11. Cope, C. L. 1972. The synthetic analogues. In Adrenal steroids and disease. Lippincott, Philadelphia, Pa. 488–491.
12. Broulik, P. D., and L. Starka. 1997. Bone 20:473–475.
13. Weinstein, R. S., and N. H. Bell. 1988. N. Engl. J. Med. 319:1698–1701.
14. Parfitt, A. M., et al. 1987. Bone histomorphometry: standardization of nomenclature, symbols, and units. Report of the ASBMR Histomorphometry Nomenclature Committee. J. Bone Miner. Res. 2:595–610.
15. Parfitt, A. M., et al. 1983. J. Clin. Invest. 72:1396–1409.
16. Bellows, C. G., et al. 1991. Bone Miner. 14:27–40.
17. Owen, M. 1985. Lineage of osteogenic cells and their relationship to the stromal system In W. A. Peck, editor. Bone and Mineral Research. Elsevier, Amsterdam, vol 3:1–25.
18. Falla, N., et al. 1993. Blood 82:3580–3591.
19. Tomkinson, A., et al. 1997. J. Clin. Endocrinol. Metab. 82:3128–3135.
20. Lynch, M. P., et al. 1998. J Cell Biochem 68: 31–49.
21. StatCorp. 1995. Stata Statistical Software Release 40. Stata Corporation, College Station, Tex., 1–1601.
22. Jilka, R. L., et al. 1992. Science 257:88–91.
23. King, C. S., et al. 1996. Calcif. Tissue Int. 59: 184–191.
24. Li, M., et al. 1996. Bone 19:81–88.
25. Quarles, L. D. 1992. Am. J. Physiol. (Endocrinol. Metab.) 263:E136–E141.
26. Grardel, B., et al. 1994. Osteoporosis Int. 4:204–210.
27. Kawai, K., et al. 1985. J. Bone Joint Surg. 67A:755–762.
28. Deloffre, P., et al. 1995. Bone 17:409S–414S.
29. Chavassieux, P., et al. 1997. Bone 20:451–455.
30. Newman, E., et al. 1995. Bone 16:277S–284S.
31. Dempster, D. W., et al. 1997. J. Endocrinol. 154:397–406.
32. Conaway, H. H., et al. 1996. J. Bone Miner. Metab. 11:1419–1429.
33. Bellows, C. G., et al. 1987. Endocrinol. 121:1985–1992.
34. Lian, J. B., et al. 1997. Endocrinol. 138:2117–2127.

35. Stanton, B., et al. 1985. J. Clin. Invest. 75:1317–1326.
36. Borchard, R. E., et al. 1992. Drug dosage in laboratory animals: a handbook. CRC Press, Inc., Boca Raton, Fla. 514–517.
37. Kleiber, M. 1961. The fire of life: an introduction to animal energetics. John Wiley & Sons, Inc. New York. Chapters 10:177–216 and 11:217–230.
38. Klein, M., et al. 1965. Acta Orthop. Scandinav. 35:171–184.
39. Bressot, C., et al. 1979. Metab. Bone Dis. & Rel. Res. 1:303–311.
40. Parfitt, A. M., et al. 1995. J. Bone Miner. Res. 10:466–473.
41. Parfitt, A. M. 1994. J. Cell. Biochem. 55:273–286.
42. Manolagas, S. C., et al. Interleukin-6-tpe cytokines and their receptors. 1996. In Principles of Bone Biology. J. P. Bilezikian, L. G. Raisz, and G. A. Rodan, editors. Academic Press, San Diego, Calif. 701–713.
43. Parfitt, A. M. 1990. Bone-forming cells in clinical conditions. I Bone: A Treatise, Vol. 1. The Osteoblast and Osteocyte. B. K. Hall, editor. Telford and CRC Press, Boca Raton, Fla. 351–429.
44. Bursch, W., et al. 1990. Carcinogenesis. 11:847–583.
45. Cline, M. J. 1974. N. Engl. J. Med. 291:1187–1188.
46. Gohel, A., and G. Gronowicz. 1997. J. Bone Miner. Res. 12 (Suppl. 1):S284. (Abstr.)
47. Frost, H. M. 1960. J. Bone Joint Surg. 42A:138–143.
48. Frost, H. M. 1960. J. Bone Joint Surg. 42A:144–150.
49. Dunstan, C. R., et al. 1993. Calcif. Tissue Int. 53:S113–117.
50. Aarden, E. M., et al. 1994. J. Cell. Biochem. 55:287–299.
51. Noble, B. S., et al. 1997. Bone 20:273–282.
52. Ficat, R. P. 1985. J. Bone Joint Surg. 67B:3–9.
53. Felson, D. T., and J. J. Anderson. 1987. Lancet 1:902–905.
54. Knight, B. et al. 1992. Clin. Exp. Immunol. 90:459–465.
55. Henriques, M. G. et al. 1987. Braz. J. Med. Biol. Res. 20: 243–249.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of screening for compounds that reduce the bone deteriorating effects of glucocorticoids, comprising the steps of:
    (a) contacting osteoblast and osteocyte cells in vitro with either a glucocorticoid alone or said glucocorticoid in combination with a test compound; and
    (b) comparing the number of osteoblast and osteocyte cells undergoing apoptosis following treatment with said glucocorticoid alone or following treatment with said glucocorticoid in combination with said test compound, wherein a lower number of apoptotic cells following treatment with said glucocorticoid in combination with said test compound than with said glucocorticoid alone indicates that the test compound reduces the bond deteriorating effects of said glucocorticoid.

2. The method of claim 1, wherein determination of apoptosis is carried out using a technique selected from the group consisting of TUNEL, DNA fragmentation and immunohistochemical analysis.

3. A method of screening for glucocorticoid analogs that possess decreased apoptotic properties towards osteoblast and osteocyte cells, comprising the steps of:
    (a) contacting said cells in vitro with either a glucocorticoid or a glucocorticoid analog; and
    (b) comparing the number of apoptotic cells following treatment with said glucocorticoid or said glucocorticoid analog, wherein a lower number of apoptotic cells following treatment with said glucocorticoid analog than with said glucocorticoid is indicative of a glucocorticoid analog that possess decreased apoptotic properties towards said cells.

4. The method of claim 3, wherein determination of apoptosis is carried out using a technique selected from the group consisting of TUNEL, DNA fragmentation and immunohistochemical analysis.

* * * * *